United States Patent [19]
Lingham et al.

[11] Patent Number: 6,110,716
[45] Date of Patent: Aug. 29, 2000

[54] HIV INTEGRASE INHIBITORS

[75] Inventors: Russell B. Lingham, Watchung, N.J.; Ali Shafiee, Westfield, N.J.; Keith C. Silverman, Somerset, N.J.; Ana M. Teran, Madrid, Spain; Sheo Bux Singh, Edison; Deborah L. Zink, Manalapan, both of N.J.

[73] Assignee: Merck & Co., Inc., Rahway, N.J.

[21] Appl. No.: 09/018,684

[22] Filed: Feb. 4, 1998

[51] Int. Cl.$^7$ .......................... A61K 31/35; C07D 311/78; C07D 321/10
[52] U.S. Cl. ........................ 435/171; 544/360; 549/267; 514/450
[58] Field of Search ........................ 514/450; 549/267; 544/360; 435/171

[56] References Cited

FOREIGN PATENT DOCUMENTS 2306476A 7/1997 United Kingdom .
WO 96/28443 9/1996 WIPO .

OTHER PUBLICATIONS

Koyama et al., Further Characterization of Seven Bis(naphtho–y–pyrone) Congeners of Ustilaginoidins, Coloring Matters of Claviceps virens (Ustilaginoidea virens), Chem. Pharm. Bull. vol. 36(1) pp. 146–152 (1988).
Koyama et al., Database HCAPLUS, Chem. Pharm. Bull, vol. 35 (10), pp. 4049–4055 (1987), No. 1988:50979 (Abstract).
Kawai et al., Database HCAPLUS on STN, No. 1992:53265, vol. 33, pp. 31–35 (1991) (Abstract).
Koyama et al., Database HCAPLUS, Chem. Pharm. Bull., vol. 36(1), pp. 146–152 (1988), No. 1988:164483 (Abstract).
Kawai et al., Database HCAPLUS on STN, No. 1992:35988, vol. 33, pp. 25–29 (1991) (Abstract).
LaFemina et al., Antimicrobial Agents & Chemotherapy, vol. 39(2), pp. 320–324 (1995), "Inhibition of human immunodeficiency virus integrase by bis–catechols".
Cushman et al., J. Med. Chem., vol. 38 (1995), pp. 443–452, "Cosalane analogues with enhanced potencies as inhibitors of HIV–1 protease and integrase".
Mazumder et al., Biochemistry, vol. 34 (1995), pp. 15111–15122, "Effects of tyrphostins, protein kinase inhibitors, on human immunodeficiency virus type 1 integrase".
Mazumder et al., J. Med. Chem., vol. 39 (1996), pp. 2472–2481, "Antiretroviral agents as inhibitors of both human immunodeficiency virus type 1 integrase and protease".
Mazumder et al., Molecular Pharmacology, vol. 49 (1996), pp. 621–628, "Effects of nucleotide analogues on human immunodeficiency virus type 1 integrase".
Kusumoto et al., C.A. 120(19):238888s, "A comparative study on the inhibitory effects of flavonoids and alkaloids on reverse transcriptases of different retroviruses", Shoyakugaku Zasshi, 47(3), pp. 291–294, 1993. (Abstract).
Mazumder et al., AIDS Research and Human Retroviruses, vol. 11(1), pp. 115–125 (1995), "Inhibition of human immunodeficiency virus type 1 integrase by a hydrophobic cation . . . ".

Mazumder et al., Proc. Nat'l Acad. Sci. USA, vol. 91, pp. 5771–5775 (1994), "Inhibition of human immunodeficiency virus type 1 integrase by 3'–azido–3'–deoxythymidylate".
Carteau et al., Archives of Biochemistry & Biophysics, vol. 305(2), pp. 606–610 (1993), "Inhibitory effect of the polyanionic drug suramin on the in vitro HIV DNA integration reaction".
Fesen et al., Proc. Nat'l Acad. Sci. USA, vol. 90 (1993), pp. 2399–2403, "Inhibitors of human immunodeficiency virus integrase".
Farnet et al., Proc. Nat'l Acad. Sci. USA, vol. 93 (1996), pp. 9742–9747, "Differential inhibition of HIV–1 preintegration complexes and purified integrase protein by small molecules".
Lutzke et al., Proc. Nat'l Acad. Sci. USA, vol. 92 (1995), pp. 11456–11460, "Identification of a hexapeptide inhibitor of the human immunodeficiency virus integrase protein by using a combinatorial chemical library".
Ojwang et al., Antimicrobial Agents & Chemotherapy, vol. 39(11), pp. 2426–2435 (1995), "T30177, an oligonucleotide stabilized by an intramolecular guanosine octet, is a potent inhibitor . . . ".
Eich et al., J. Med. Chem., vol. 39 (1996), pp. 86–95, "(–)–Arctigenin as a lead structure for inhibitors of human immunodeficiency virus type–1 integrase".
Robinson, Jr., et al., Proc. Nat'l Acad. Sci. USA, vol. 93 (1996), pp. 6326–6331, "Inhibitors of HIV–1 replication that inhibit HIV integrase".
PRNewswire, Sep. 17, 1996, "Aronex reports results for lead anti–HIV integrase inhibitor compound".
Neamati et al., "Design and discovery of HIV–1 integrase inhibitors", DDT 2(11) (1997), pp. 487–498.
Hazuda et al., Nucleic Acids Research, vol. 22 (6), pp. 1121–1122 (1994), "A novel assay for the DNA strand–transfer reaction of HIV–1 integrase".
Burke et al., J. Med. Chem., vol. 38 (1995), pp. 4171–4178, "Hydroxylated aromatic inhibitors of HIV–1 integrase".
Hazuda et al., J. of Virology, vol. 71(1), pp. 807–811 (1997), "Equivalent inhibition of half–site and full–site retroviral strand transfer reactions by structurally diverse compounds".
Fesen et al., Biochemical Pharma., vol. 48(3), pp. 595–608 (1994), "Inhibition of HIV–1 integrase by flavones, caffeic acid phenethyl ester (cape) and related compounds".
Koyama et al., Chem. Pharm. Bull., 36(1), 146–152. 1988.
Mori et al., Mycotoxin Research, vol. 9, 85–93, 1993.
Koyama et al., Tennen Yuki Kagobutsu Toronkai Koen Yoshishu, 29, 713–720, 1987.

*Primary Examiner*—Johann Richter
*Assistant Examiner*—Taofiq A. Solola
*Attorney, Agent, or Firm*—Catherine D. Fitch; Kenneth R. Walton; Melvin Winokur

[57] ABSTRACT

Natural products such as certain chaetochromins are described. These compounds are useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

17 Claims, No Drawings

HIV INTEGRASE INHIBITORS

CROSS REFERENCE TO RELATED APPLICATIONS

The present application claims priority of U.S. provisional application Ser. No. 60/036,902, filed Feb. 6, 1997, now abandoned.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid cells. Integration is believed to occur in three stages: cleavage of two nucleotides from the 3' termini of the linear proviral DNA; covalent joining of the recessed 3' OH termini of the proviral DNA at a staggered cut made at the host target site; repair synthesis by host enzymes.

Nucleotide sequencing of HIV shows the presence of a pol gene in one open reading frame [Ratner, L. et al., Nature, 313, 227 (1985)]. Amino acid sequence homology provides evidence that the pol sequence encodes reverse transcriptase, an integrase and an HIV protease [Toh, H. et al., EMBO J. 4, 1267 (1985). Power, M. D. et al., Science, 231, 1567 (1986); Pearl, L. H. et al., Nature 329,351 (1987)].

It is known that some antiviral compounds act as inhibitors of HIV and are effective agents in the treatment of HIV and similar diseases, e.g., azidothymidine or AZT. Applicants demonstrate that the compounds of this invention are inhibitors of HIV integrase, probably by inhibiting strand transfer and cleavage activity. The particular advantage of the present invention is specific inhibition of HIV integrase.

Applicants have discovered that certain chaetochromins are potent inhibitors of HIV integrase. These compounds are useful for the treatment of AIDS or HIV infections.

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of formula I are defined as follows:

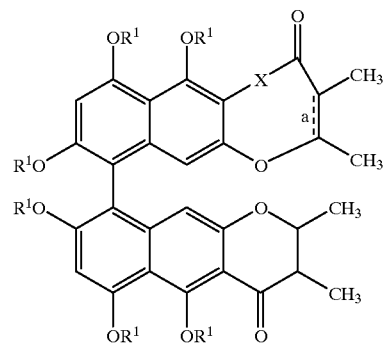

(I)

wherein:

$R^1$ is independently selected from:
  (a) hydrogen,
  (b) $C_{1-6}$ alkyl, and
  (c) $C_{1-6}$ alkylcarbonyl-
at each occurrence;

—X— is selected from:
  (a) a carbon-carbon single bond, and
  (b) an oxygen atom bound to adjacent carbon atoms;
  and the dotted line, a, is represents a single bond or a double bond;

or a pharmaceutically acceptable salt thereof.

In one embodiment of compounds-of the present invention are compounds of structural formula (I) wherein:

$R^1$ is independently selected from:
  (a) hydrogen,
  (b) methyl, and
  (c) methylcarbonyl-
at each occurrence, or a pharmaceutically acceptable salt thereof.

Compounds representing this embodiment include:

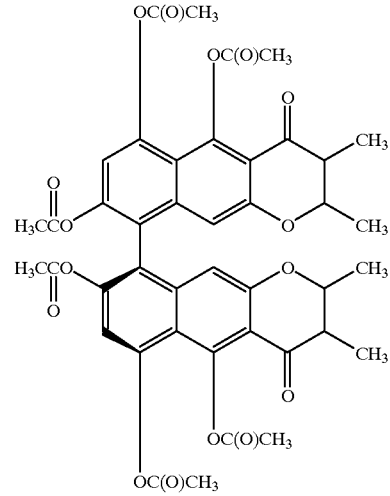

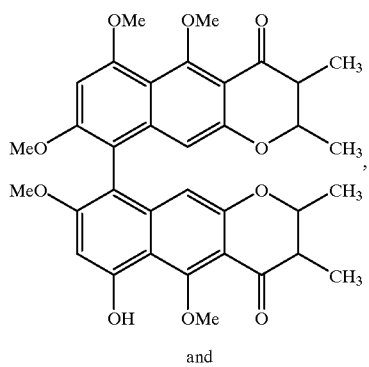

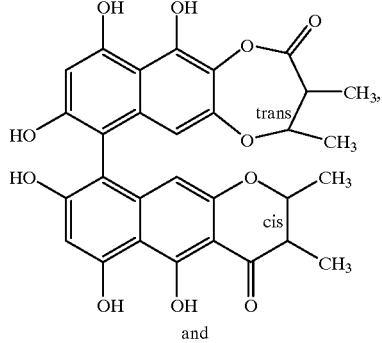

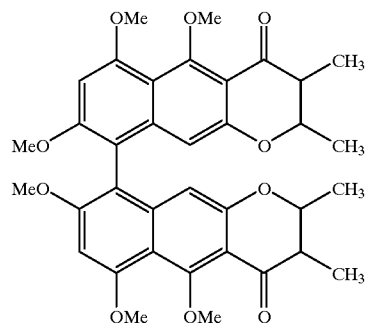

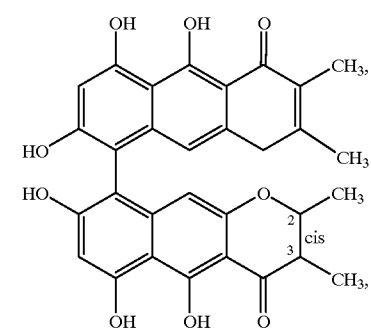

In one subclass of compounds of the present invention are ocmpounds of structural formula (I) wherein $R^1$ is hydrogen at each occurrence, or a pharmaceutically acceptable salt thereof.

Compounds illustrating this subclass are:

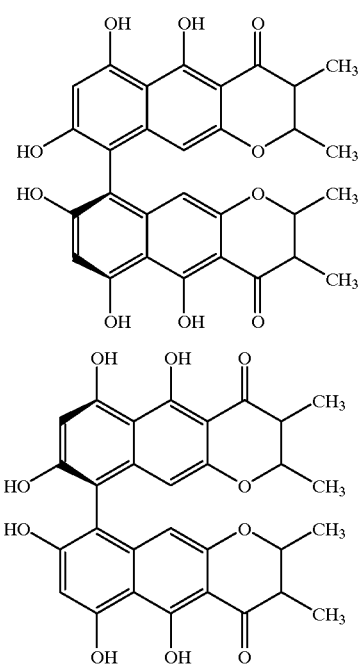

or pharmaceutically acceptable salts thereof.

Also covered by the present invention are pharmaceutical compositions useful for inhibiting HIV integrase, comprising an effective amount of a compound of this invention. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. This invention also discloses the fungal culture MF6252 (ATCC 74396), Fusarium sp.

The present invention relates to the preparation of compounds of structural formula I comprising:

(a) fermenting a culture of MF6252 (ATCC 74396), Fusarium sp. or a mutant thereof to produce a fermentation broth, (b) extracting the fermentation broth with an organic solvent, (c) isolating the compounds of structural formula I.

The compounds of structural formula I are preferably isolated by partitioning the fermentation extract between the organic solvent and water, followed by size exclusion chromatography and normal or reverse-phase chromatography.

When any variable (e.g., X, Y, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

Applicants have discovered that certain chaetochromins, recovered from a fungal culture of MF6252 (ATCC 74396), identified as Fusarium sp. (Ascomycotina, Hypocreales), are useful for inhibiting HIV integrase. The compounds of formula (I) are prepared by an aerobic fermentation procedure employing a novel fungal culture MF6252 (ATCC 74396), identified as Fusarium sp., or a mutant thereof. A mutant refers to an organism in which some gene on the genome is modified, leaving the gene or genes responsible for the organism's ability to produce the compounds of formula (I) in recoverable amounts functional and heritable. ATCC Deposit of MF6252 (ATCC 74396), identified as Fusarium sp.

Before the U.S. filing date of the present application, a sample of MF6252 (ATCC 74396), Fusarium sp., had been deposited at the American Type Culture Collection (ATCC), 12301 Parklawn Drive, Rockville, Md. 20852. The culture access designation is 74396. This deposit will be maintained in the ATCC for at least 30 years and will be made available to the public upon the grant of a patent disclosing it. It should be understood that the availability of a deposit does not constitute a license to practice the subject invention in derogation of patent rights granted by government action. Characteristics of MF6252 (ATCC 74396), Fusarium sp.

Isolated from forest leaf litter, Te Anau, South Island of New Zealand.

In agar culture MF6252=ATCC 74396 exhibits the following characteristics. Observations of micromorphology were made on 1 week-old colonies grown on SNA unless stated otherwise.

Colonies on SNA (Synthetischer Nährstoffarmer agar; Gerlach, W. and Nirenberg, H. 1982. The genus Fusarium—a pictorial atlas. Milleilungen aus der Biologische Bundesanstalt für Land- und Forstwirtschaft, Berlin-Dahlem 209: 1-406) at 25° C., 12 hr photoperiod attaining 25–26 mm after 7 days, translucent, faintly zonate, mycelium most appressed or submerged, with some scant moist conidial pustules surrounding inoculation point Colonies on oatmeal agar (Difco Laboratories) at 25° C., 12 hr photoperiod attaining 24–25 mm after 7 days, developing pronounced moist radial hyphal strands, floccose to plumose, with margin even, submerged, with aerial mycelium white to pale peach-colored, Pale Ochraceous-Buff, Light Buff (capitalized color names from Ridgway, R. 1912. Color Standards and Nomenclature, Washington, D.C.), basal mycelium yellowish green, Primrose Yellow to near Olive-Yellow. After one month, strongly radially plumose, zone, white to yellowish green. No growth on oatmeal agar at 37° C.

Colonies on potato dextrose agar (Difco Laboratories) at 25° C., 12 hr photoperiod, attaining 19–20 mm after 7 days, with wide, submerged or moist margin, quickly developing strong radial, semi-erect hyphal strands, dull peach colored to yellowish green, Light Buff, Napthalene Yellow, buff to dull olive, Cream-Buff to near Yellowish Olive, in reverse.

Conidiophores, conidiogenous cells and conidia are of two different states; an Acremonium-like microconidial state which is the dominant form on SNA; and a macroconidial state which on SNA is restricted to pinnotes in the area immediately surrounding the inoculation point, on other media, e.g. potato-dextrose agar, the macroconidial form is produced throughout the colony.

Microconidial state: Microconidiophores 25–70 $\mu$m long× 2.5–4 $\mu$m wide at the base, septate at the base, rarely 2- or 3-septate, mostly unbranched, tapered upward, straight to slightly geniculate, scattered to densely clustered on both the surface and aerial hyphae, terminating in a cylidrical to flared collarette, with slight periclinal thickening evident on some conidiogenesis cells, enteroblastic, phialidic. Microcondia for the most part distinct from macroconidia, 3.5–6× 2–3 $\mu$m, narrowly ellipsoidal to allantoid.

Macroconidial state: Macroconidiophores aggregated in pinnotes, consisting of penicillately branched fascicles of conidiogenous cells. Conidiogenous cells cylindrical or tapered apically, without collarettes, sometimes with slight periclinal thickenings at conidiogenous loci, with individual conidiogenous cells up to 35 $\mu$m long. Macroconidia 10–50 $\mu$m×3.5–5 $\mu$m 1–6 septate, predominantly 3-septate, fusiform curved, with apical cell rounded, with slightly pedicellate foot cell, often the apical or subapical cells more curved than the more proximal cells.

Chlamydospores and sclerotia not in observed in PDA or OA cultures incubated up to 5 weeks.

This fungus is assigned the anamorph genus Fusarium because it produces moist, fusoid, curved, septate conidia with a pedicellate foot cell from phialidic conidiogenous cells. This isolate possibly belongs in the Section Martiella of Fusarium (as defined by C. Booth. 1971. The genus Fusarium. Commonwealth Mycological Institute, Kew, U.K., pg. 44), due to its abundant Acremonium-like conidial state, penicillate macrocroconidial state, macroconidia with blunt rounded apices, pale to yellow or greenish yellow pigments, and moderate growth rate. The absence of chlamydospores has been noted in some species of the section Martiella e.g. *F. illudans* and the Fusarium state of *Nectria borneensis* (Samuels, G. J., Y. Doi, and C. T. Rogerson. 1990. Memoirs of the New York Botanical Garden 59: 47–48).

In general, MF6252 (ATCC 74396), identified as Fusarium sp. is cultured on a solid medium, or in an aqueous nutrient medium containing sources of assimilable carbon and nitrogen. For example, the cultures can be grown under submerged aerobic conditions (e.g., shaking culture, submerged culture, etc.) The aqueous medium is preferably maintained at a pH of about 6–8 at the initiation and termination (harvest) of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, sucrose, dextrin, and the like. Other cources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions is one method of culturing the cells. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 6–7 to the autoclaving step.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably 22–25° C., for a period of about 14–21 days, which may be varied according to fermentation conditions and scales.

Preferred culturing/production media for carrying out the fermentation include the media as set forth in the Examples.

After growth is completed, the cells are harvested by conventional methods, e.g., centrifugation and filtration, and then extracted with the appropriate solvent, e.g., methylethylketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate was separated and concentrated to dryness initially by evaporating under reduced pressure followed by lyophilization. The compounds were finally isolated either by solvent partitioning and crystallization or by preparative HPLC on reversed phase systems.

Compounds of formula (I) may be isolated from the aerobic fermentation of a culture of MF6252 (ATCC 74396), Fusarium sp.. A culture of MF6252 (ATCC 74396) is defined as substantially free of its natural soil contaminants and capable of forming compounds of structural formula (I) in recoverable amounts. The culture employed in the present invention should be free from viable contaminating microorganisms deleterious to the production of the compound of structural formula (I). A biologically pure culture of MF6252 (ATCC 74396) may also be employed.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting the free acid with a suitable organic or inorganic base.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results directly, or indirectly, from combination of the specified ingredients in the specified amounts.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| Indinavir | Merck (Rahway, NJ) | AIDS, ARC, asymptomatic HIV positive, also in combination with AZT. |
| Nevirapine | Boeheringer Ingleheim | AIDS, ARC (protease inhibitor) |
| Delaviridine | Pharmacia-Upjohn | AIDS, ARC (protease inhibitor) |
| Ritonavir | Abbott | AIDS, ARC (protease inhibitor) |
| Saquinavir | Hoffmann-LaRoche | AIDS, ARC (protease inhibitor) |
| Nelfinavir | Agouron Pharmaceuticals | AIDS, ARC (protease inhibitor) |
| 141 W94 | Glaxo-Wellcome | AIDS, ARC (protease inhibitor) |
| DMP-266 | DuPont-Merck Pharmaceuticals | AIDS, ARC (non-nucleoside reverse |

-continued

| Drug Name | Manufacturer | Indication |
|---|---|---|
| | | transcriptase inhibitor) |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246, 738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F 106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with | Upjohn | PCP |

| Drug Name | Manufacturer | Indication |
|---|---|---|
| Primaquine | (Kalamazoo, MI) | |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg, three times a day.

EXAMPLE 1

Fermentation

A. Media:

Seed medium contained the following in g/L: corn steep liquor, 5 g; tomato paste, 40; oat flour, 10; glucose, 10; agar, 4; $FeSO_4 \cdot 7H_2O$, 0.01; $MnSO_4 \cdot 4H_2O$, 0.01; $CuCl_2 \cdot 2H_2O$, 0.00025; $CaCl_2$, 0.001; $H_3BO_3$, 0.00056; $(NH_4)_6Mo_7O_{24} \cdot 4H_2O$, 0.00019; $ZnSO_4 \cdot 7H_2O$, 0.002. The pH was adjusted to 6.8.

Production media contained the following in grams per liter: sucrose, 80; yellow corn meal, 50; yeast extract, 1.

B. Inoculum Preparation:

Frozen vegetative mycelia (FVM) were prepared by inoculating 50 mL of seed medium in a 250 mL flask and incubating at 25° C., 85% relative humidity and at 200 rpm for 3–5 days. Aliquots of the culture were frozen and used as a source of inoculum for future experiments.

C. Seed Culture:

To 50 mL of seed media in a 250 mL flask, 2.0 mL of FVM was added as inoculum and the flasks were incubated at 25° C., 8% relative humidity and at 200 rpm for 2–3 days.

D. Production Culture and Extraction:

To 50 mL of production media in a 250 mL flask, 1 mL of seed culture was added as inoculum and the flasks were incubated at 25° C., 85% relative humidity and at 200 rpm for 21 days. Each flask was then extracted with 50 mL of methyl ethyl ketone and the solids were discarded.

EXAMPLE 2

Isolation and Characterizations of Compounds A and B

I: First Isolation

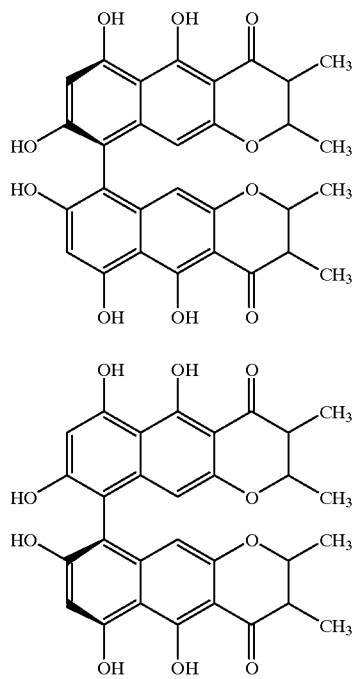

Compound A

Compound B

Five mL of fermentation broth of culture MF6252 (ATCC 74396) was extracted with 50 mL of methyl ethyl ketone to give yellowish green extract. The extract was concentrated under reduced pressure to remove most of the methyl ethyl ketone followed by lyophilization to give 40 mg of viscous greenish gum. This gummy material was chromatographed over a SEPHADEX LH-20 column (200 mL). The material was charged in methanol-methylene chloride (5 mL, 1:1) and the column was eluted with methanol. The HIV-integrase activity eluted in a broad zone and the fractions that showed activity against HIV-integrase were combined and chromatographed on a ZORBAX RX C-8 (22×250 mm) reverse phase column. The compounds were eluted from the column with a 60 minutes linear gradient of 50 to 90% aqueous acetonitrile containing 0.1% trifluoroacetic acid at a flow rate of 10 mL per minute. The elution of the column was monitored by a in-line ultraviolet detection at 250 nm. Fractions eluting at 27 and 28 minutes were concentrated and subsequently lyophilized to give compound A and compound B, respectively, as yellow powders.

The purity of these compounds was evaluated by an analytical HPLC using ZORBAX RX C-8 (4.6×250 mm) column eluting at a flow rate of 1 mL per minute with 65% aqueous acetonitrile (+0.1 % TFA). compound A eluted at a retention time of 8.1 minute and compound B eluted at a retention time of 9.0 minutes. These compounds are members of chaetochromin/ustilaginoidin family. One set of the methyl groups in each of these compounds is cis and the other set is trans. Atropisomers were assigned based on the comparison of the optical rotation values. Chaetochromin B ($[\alpha]_D$+524, ref Koyama & Natori Chem. Pharm. Bull. vol 35, pp 578–584, 1987) has same gross structure as A ($[\alpha]_D$+827) and B ($[\alpha]_D$–188) except for stereo-chemistry. Both of these compounds are nonsymmetrical dimers.

II. Second Isolation

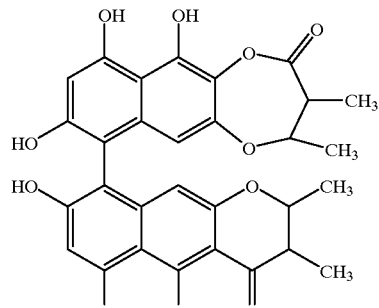

C

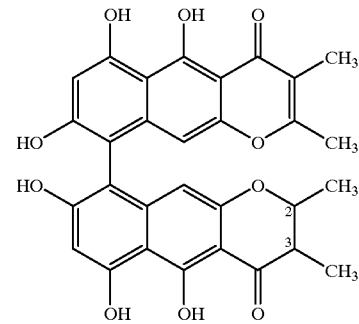

D

A 1.2 L regrowth of MF6252 (ATCC 74396) was extracted with methyl ethyl ketone to give an 850 mL extract that was concentrated as described above in part I, First Isolation. The dark semi solid thus obtained was dissolved in methanol-acetone (4:1, 250 mL) and was filtered. The filtrate was similarly chromatographed over a SEPHADEX LH-20 column and column was eluted with methanol. The fractions were evaluated by TLC (silica gel, Methylene chloride-Methanol, 92/8+0.1% AcOH). The fraction eluting from 2500 mL to 3000 mL of elution volume of methanol were combined and concentrated to give fraction A; fractions from 3001 to 4100 mL elution volume of methanol gave fraction B and 4001 mL to 6000 mL gave fraction C.

A 75 mg portion of fraction A was dissolved in 0.5 mL acetonitrile and was chromatographed over a ZORBAX RX C-8 (22×250 mm) reverse phase column and eluted with a 60 minutes gradient of 40 to 60% aqueous acetonitrile containing 0.1% TFA at a flow rate of 10 mL per minute. The elution was detected by 210 nm in-line ultra violet light. The fractions eluting between 34 to 38 minutes were combined, concentrated under reduced pressure, and lyophilized to give compound C as a yellow powder.

Fraction B (1.0 g) was chromatographed on a silica gel column (3×20 cm). The column was packed in and washed with methylene chloride and the material was loaded in a 1:1 mixture of methylene chloride - acetone. Elution of the column with 4% methanol in methylene chloride containing 0.1% acetic acid and concentration of the fractions gave compound B as yellow powder.

Fraction C (50 mg) was dissolved in 0.5 mL acetonitrile and was chromatographed on a similar ZORBAX RX C-8 column. Elution of the column at 10 mL per minute with a 80 minute step gradient of aqueous acetonitrile containing 0.1% TFA. The gradient was as follows: 50% aqueous acetonitrile for 10 minute, 50 to 70% (10.01 to 70 minute) and 70 to 100% (70.01 to 80 minute). The fractions eluting between 46–47 minutes were combined, concentrated and lyophilized to give compound D as a yellow powder. Compound C has 2,3-trans and 2',3'-cis stereochemistry. Compound D has a 2,3-Cis stereochemistry.

EXAMPLE 3

Physical and Spectral Properties:

I. Compound A:
Mass spectra: HREIMS (m/z): 546.1505 (M+, calcd. for $C_{30}H_{26}O_{10}$: 546.1525).
Specific rotation: $[\alpha]^{25}_D$=+827 (c, 0.13, MeOH)
NMR Spectra: See Tables 1 and 2.

II. Compound B:
Mass spectra: HREIMS (m/z): 546.1501 (M+, calcd. for $C_{30}H_{26}O_{10}$: 546.1525).
Specific rotation: $[\alpha]^{25}_D$=−188 (c, 0.13, MeOH)
NMR Spectra: See Tables 1 and 2.

III. Compound C:
Mass spectra: HREIMS (m/z): 562.1458 (M+, calcd. for $C_{30}H_{26}O_{11}$: 562.1475).
NMR Spectra: See Table 3.

IV. Compound D:
Mass spectra: HREIMS (m/z): 544.1365 (M+, calcd. for $C_{30}H_{24}O_{10}$: 544.1369).
NMR Spectra: See Table 2.

$^{13}C$ NMR and $^1H$ NMR

All of the NMR spectra were recorded on a Varian Unity 400 or a Varian 300 MHz spectrometers operating at a field strength of 400 MHz and 300 MHz for proton NMR, 100 and 75 MHz for carbon NMR respectively. The data are summarized in following Tables. The coupling constant, J, is expressed in Hz.

Table 1: $^{13}C$ NMR Assignment of Compound A and Compound B in CDCl3 at 75 MHz.

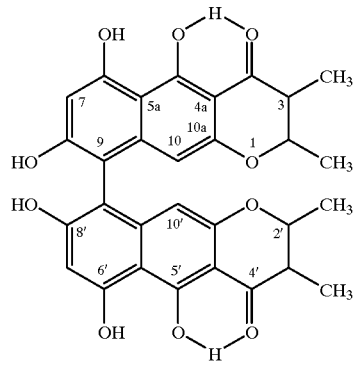

| Carbon # | Compound A (δC) | Compound B (δC) |
|---|---|---|
| 2, 2' | 78.4, 75.6 | 78.4, 75.6 |
| 3, 3' | 46.1, 44.4 | 46.2, 44.4 |

-continued

| Carbon # | Compound A (δC) | Compound B (δC) |
|---|---|---|
| 4, 4' | 202.3, 200.7 | 202.3, 200.7 |
| 4a, 4a' | 101.5, 101.4 | 101.5, 101.4 |
| 5, 5' | 165.6, 164.7 | 165.6, 164.7 |
| 5a, 5a' | 105.6, 105.1 | 105.6, 105.0 |
| 6, 6' | 158.5, 158.3 | 158.6, 158.2 |
| 7, 7' | 100.1, 99.8 | 100.1, 99.9 |
| 8, 8' | 161.1, 159.5 | 161.1, 159.7 |
| 9, 9' | 102.1, 102.0 | 102.4, 102.0 |
| 9a, 9a' | 142.6, 141.3 | 142.6, 141.2 |
| 10, 10' | 99.0, 99.0 | 99.1, 99.1 |
| 10a, 10a' | 156.1, 155.5 | 156.2, 155.4 |
| 2-CH3, 2'-CH3 | 19.7, 16.6 | 19.7, 16.5 |
| 3-CH3, 3'-CH3 | 10.2, 9.7 | 10.0, 9.7 |

TABLE 2

$^1H$ NMR Assignment of Compound A; Compound B and Compound D in CDCl3

| Proton # | Compound A δH (J values in Hz) in CDCl3 (300 MHz) | Compound B δH (J values in Hz) in CDCl3 (300 MHz) | Compound D δH (J values in Hz) in CD3CN (400 MHz) |
|---|---|---|---|
| 2,2' | 4.17, dq, J = 10.8, 6.3 | 4.14, dq, J = 11.1, 6.3 | 4.65, dq, J = 3.0, 6.4 |
|  | 4.64, dq, J = 3.0, 6.6 | 4.62, dq, J = 3.0, 6.6 |  |
| 3,3' | 2.75, dq, J = 3.0, 7.0 | 2.72, dq, J = 3.0, 7.5 | 2.80, dq, J = 2.4, 7.3 |
|  | 2.66, dq, J = 6.9, 10.8 | 2.66, dq, J = 6.9, 10.8 |  |
| 7,7' | 6.55, s | 6.56, s | 6.54, s |
|  | 6.57, s | 6.56, s | 6.48, s |
| 10, 10' | 6.15, s | 6.13, s | 6.42, s |
|  | 6.75, s | 6.72, s | 6.68, s |
| 2-CH3 | 1.44, d, J = 6.6 Hz | 1.43, d, J = 6.3 | 1.37, d, J = 6.8 |
| 2'-CH3 | 1.44, d, J = 6.6 Hz | 1.43, d, J = 6.3 | 2.29, s |
| 3-CH3 | 1.26, d, J = 7.5 Hz | 1.26, d, J = 7.2 | 1.26, d, J = 7.2 |
| 3'-CH3 | 1.25, d, J = 7.2 Hz | 1.23, d, J = 6.9 | 1.96, s |
| 5-OH, 5'-OH | 15.53, s; 15,39, s | 15.48, s; 15.36, s | 16.64, s; 15.64, s |
| 6-OH, 6'-OH | 9.93, s; 9.77, s | 9.93, s; 9.76, s | 9.94, s; 9.72, s |
| 8-OH, 4'-OH | 5.49, brs; 5.28, brs | 5.69, brs; 5.29, brs | 5.69, brs; 5.29, brs |

TABLE 3

$^1$H and $^{13}$C NMR Assignment of Compound C in a mixture of CDCl$_3$ and CD$_3$CN at 400 MHz at 25° C.

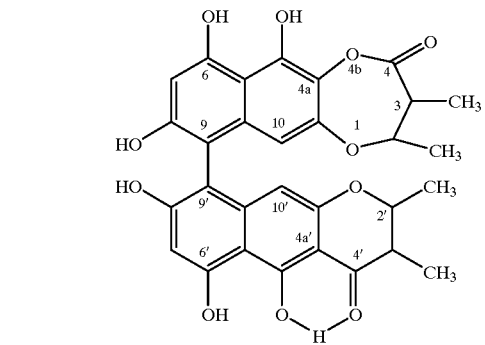

| Carbon # | δC | δH (1:1 CDCl$_3$/CD$_3$CN) | δH (4:1 CDCl$_3$/CD$_3$CN) |
|---|---|---|---|
| 2 | 82.6 | 4.33, m | 4.15, dq, J = 10.4, 6.4 |
| 2' | 74.7 | 4.62, dq, J = 3.6, 6.4 | 4.42, dq, J = 3.6, 6.8 |
| 3 | 41.2 | 2.86, m | 2.67, dq, J = 10.8, 6.4 |
| 3' | 43.1 | 2.77, dq, J = 3.6, 6.8 | 2.55, dq, J = 3.26, 6.0 |
| 4 | 170.9 | — | — |
| 4' | 201.3 | — | — |
| 4a | 126.6* | — | — |
| 4a' | 100.2 | — | — |
| 5 | 142.4 | — | — |
| 5' | 165.0 | — | — |
| 5a | 107.6 | — | — |
| 5a' | 103.9 | — | — |
| 6 | 154.5 | — | — |
| 6' | 157.2 | — | — |
| 7 | 100.4 | 6.53, s | 6.37, s |
| 7' | 100.9 | 6.62, s | 6.45, s |
| 8 | 153.3 | — | — |
| 8' | 159.4 | — | — |
| 9 | 102.6 | — | — |
| 9' | 104.4 | — | — |
| 9a | 132.6* | — | — |
| 9a' | 141.3 | — | — |
| 10 | 108.6 | 6.40, s | 6.24, s |
| 10' | 99.8 | 6.48, s | 6.32, s |
| 10a | 142.9 | — | — |
| 10a' | 154.2 | — | — |
| 2-CH$_3$ | 16.5 | 1.15, d, J = 6.0 | 0.99, d, J = 6.4 |
| 2'-CH$_3$ | 15.3 | 1.36, d, J = 6.4 | 1.19, d, J = 6.8 |
| 3-CH$_3$ | 12.1 | 1.06, d, J = 6.8 | 0.91, d, J = 6.4 |
| 3'-CH$_3$ | 8.43 | 1.18, d, J = 7.2 | 1.02, d, J = 7.2 |
| 5-OH | — | — | — |
| 5'-OH | — | 15.6, s | 15.5, s |
| 6-OH | — | — | — |
| 6'-OH | — | 9.7, s | 9.6, s |
| 8-OH | — | — | — |
| 8'-OH | — | — | — |

EXAMPLE 4

Acetylation of compound B:

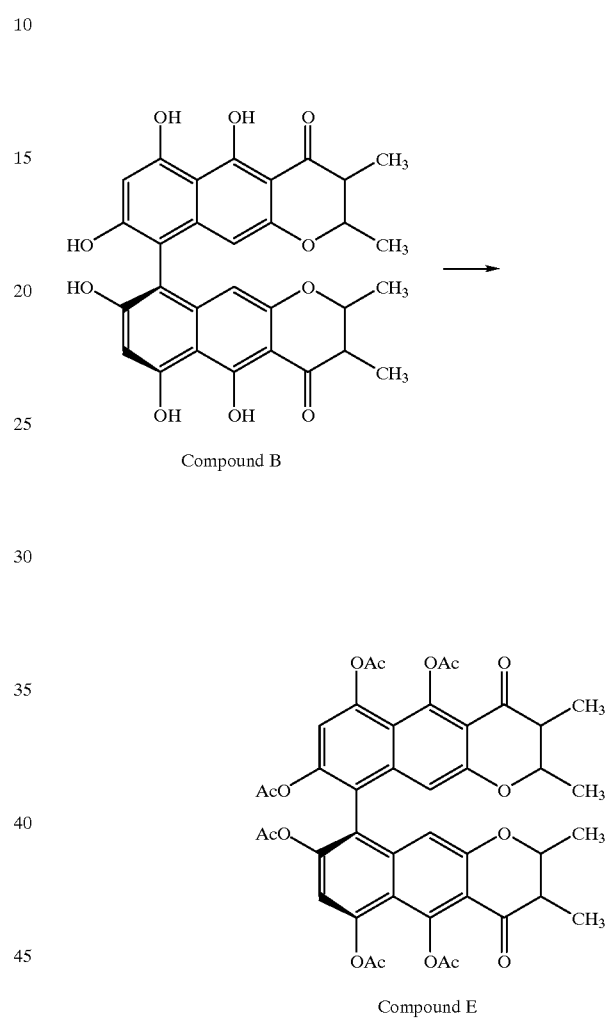

To a solution of compound B (20 mg) in pyrid ML) was added 0.5 mL acetic anhydride. The solution was stirred at room temperature overnight. Methanol was added to the reaction mixture and was concentrated under reduced pressure to dryness. The product was purified by preparative silica gel TLC (hexane-EtOAc, 3:7) and the major yellow band was eluted with 2% methanol in EtOAc to give hexaacetate (compound E) of compound B as a pale powder. HREIMS (m/z): 798 (15%, M+), $^1$NMR (δ in CDCl$_3$ at 60° C.): 1.16 (3H, d, J=6.8 Hz, CH$_3$), 1.18 (3H, d, J=6.8 Hz, CH$_3$), 1.41 (3H, d, J=6.8 Hz, CH$_3$), 1.43 (3H, d, J=6.8 Hz, CH$_3$), 1.74 (3H, s, CH$_3$), 1.85 (3H, s, CH$_3$), 2.03 (3H, s, CH$_3$), 2.39 (3H, s, CH$_3$), 2.40 (3H, s, CH$_3$), 2.50 (3H, s, CH$_3$), 2.59 (1H, m, CH), 2.78 (1H, m, CH), 4.22 (1H, m, CH), 4.70 (1H, m, CH), 6.87 (1H, s, CH), 7.00 (1H, s, CH), 7.32 (1H, s, CH), 7.54 (1H, s, CH).

EXAMPLE 5

Methylation of Compound B to form Compounds F and G

EXAMPLE 6

HIV Integrase Substrate Cleavage

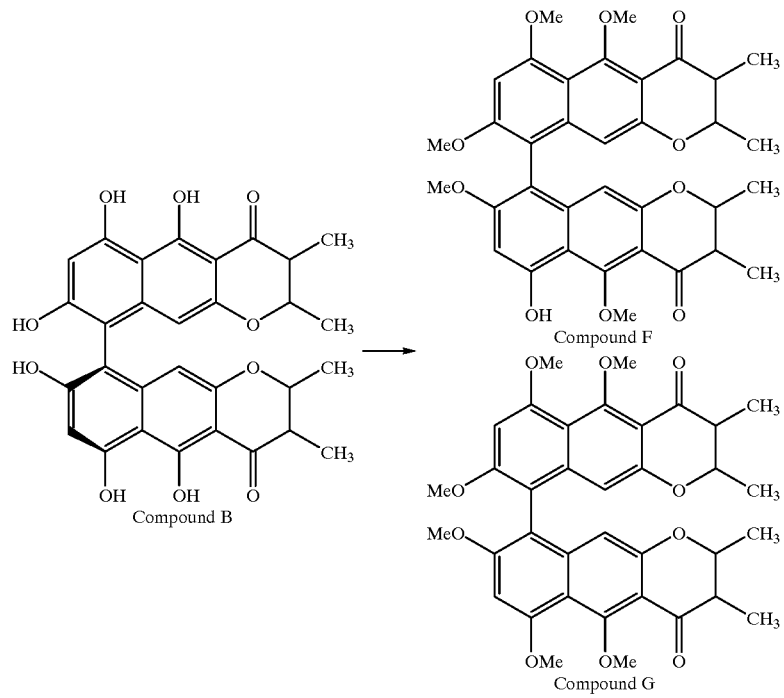

To a cooled (0° C.) solution of compound B (20 mg) in 1 mL methylene chloride was added an excess of freshly prepared solution of diazomethane in methylene chloride. The solution was stirred at room temperature overnight. Additional diazomethane was added and the solution was allowed to stir another 24 hrs. HPLC analysis (ZORBAX RX C-8, 4.6×250 mm, 70% aqueous acetonitrile +0.1% TFA, 1 mL per minute) indicated formation of two major compounds. Volatile materials were removed under a stream of nitrogen and the products were purified on a ZORBAX RX C-8 (22×250 mm) column. The compounds were eluted isocratically for 30 minutes with 60% aqueous acetonitrile containing 0.1% TFA followed by a gradient to 75% over 30 minutes. The flow rate was 10 mL per minute. Fractions eluting between 30 to 32, and 34 to 36 minutes were combined and lyophilized to give penta- (Compound F) and hexamethyl (Compound G) ethers, respectively, as yellow powders.

Compound F: EIMS (m/z): 616 (100%, M+),$^1$NMR ($\delta$ in CDCl$_3$ at 25° C.): 1.17(3H, d, J=6.8Hz,CH$_3$),1.21(3H, d, J=7.2Hz, CH$_3$),1.40 (3H, d, J=6.0 Hz, CH$_3$),1.44 (3H, d, J=6.4 Hz, CH$_3$),2.52 (1H, m, CH), 2.70 (1H, m, CH), 3.77 (3H, s, CH$_3$),3.86 (3H, s, CH$_3$),3.97 (3H, s, CH$_3$),4.04 (3H, s, CH$_3$),4.07 (3H, s, CH$_3$),4.12 (1H, m, CH), 4.66 (1H, m, CH), 6.56 (1H, s, CH), 6.62 (1H, s, CH), 6.63 (1H, s, CH), 7.02 (1H, s, OH).

Compound G: EIMS (m/z): 630 (100%, M+), $^1$NMR ($\delta$ in CDCl$_3$ at 25° C.): 1.17 (3H, d, J=6.8 Hz, CH$_3$),1.22 (3H, d, J=7.2 Hz, CH$_3$),1.38 (3H, d, J=6.4 Hz, CH$_3$),1.42 (3H, d, J=6.4 Hz, CH$_3$),2.52 (1H, m, CH), 2.77 (1H, m, CH), 3.50 (3H, s, CH$_3$),3.75 (3H, s, CH$_3$),3.84 (3H, S, CH$_3$), 3.94 (3H, s, CH$_3$), 3.98 (3H, s, CH$_3$),4.06 (3H, s, CH$_3$), 4.12 (1H, m, CH), 4.66 (1H, m, CH), 6.49 (1H, s, CH), 6.61 (1H, s, CH), 6.84 (1H, s, CH), 7.06 (1H, s, CH).

An assay for trimming of the 3' and of HIV long terminal repeat terminus by HIV-1 integrase was conducted according to LaFemina, R. L. et al., J. Virol 10, 5624 (1991), herein incorporated by reference for these purposes. To assay inhibition of HIV integrase substrate cleavage, the reaction was conducted with inhibitor having various concentrations in the range of 0.75 to 100 $\mu$M. Results follow:

| Compound | IC$_{50}$ |
|---|---|
| A | 2 $\mu$M |
| B | 2 $\mu$M |
| C | 3 $\mu$M |
| D | 1 $\mu$M |
| E | 50 $\mu$M |
| F | 40 $\mu$M |
| G | 60 $\mu$M |

EXAMPLE 7

Strand Transfer Assay for HIV Integrase

A microtiter assay for ligation of processed donor (HIV) DNA to unspecific, nicked host DNA was conducted according to Hazuda, D. J. et al., Nucl. Acids, Res. 22, 1121 (1994), herein incorporated by reference for these purposes. To assay inhibition of such strand transfer by HIV integrase, the reaction was conducted with inhibition having various concentrations in the range of 0.75 to 100 $\mu$M. Representative results follow.

| Compound | IC$_{50}$ |
|----------|-----------|
| A | 12 μM |
| B | 12 μM |
| C | 9 μM |
| D | 4 μM |

EXAMPLE 8

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed:

1. A compound selected from:

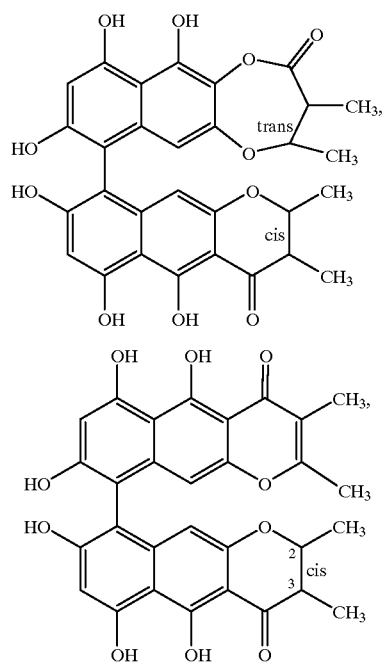

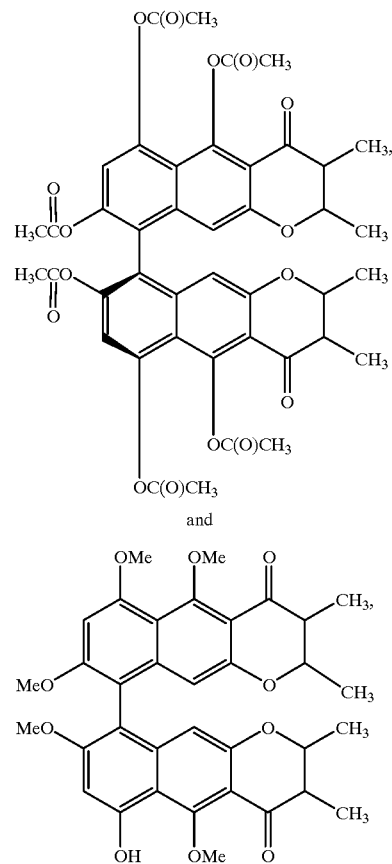

or a pharmaceutically acceptable salt thereof.

2. The compound according to claim 1 selected from:

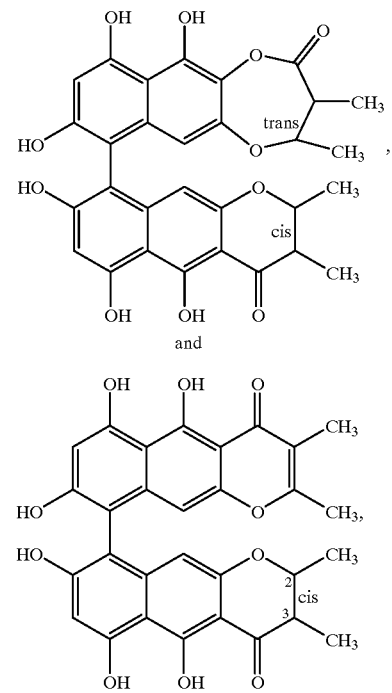

or pharmaceutically acceptable salts thereof.

3. The compound according to claim 1 selected from:

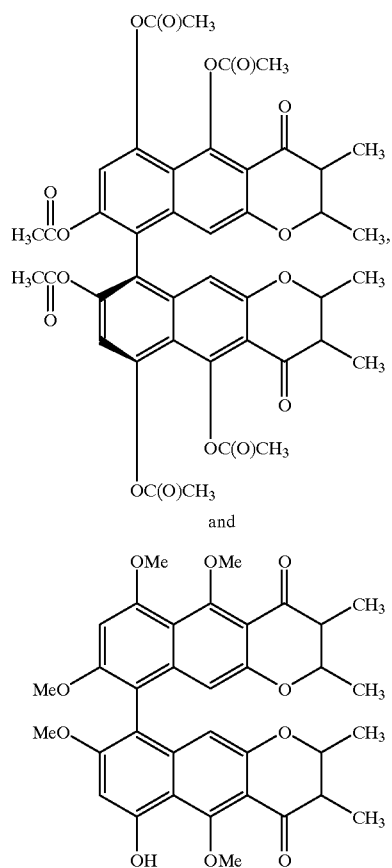

and

4. A pharmaceutical composition comprising a therapeutically effective amount of a compound according to claim 1 and a pharmaceutically acceptable carrier.

5. A pharmaceutical composition comprising a therapeutically effective amount of a compound of claim 1 in combination with a therapeutically effective amount of an AIDS treatment agent selected from:

(a) an AIDS antiviral agent, (b) an immunomodulator, and (c) an anti-infective agent.

6. The pharmaceutical composition according to claim 5 wherein the AIDS antiviral agent is:

N-(2(R)-hydroxy-1(S)-indanyl)-2(R)-phenylmethyl-4(S)-hydroxy-5-( 1-(4-( 3-pyridylmethyl)-2(S)-N'-(t-butylcarboxamido)-piperazinyl))-pentaneamide, or a pharmaceutically acceptable salt thereof.

7. A pharmaceutical composition made by combining the compound of claim 1 and a pharmaceutically acceptable carrier.

8. A process for making a pharmaceutical composition comprising combining a compound of claim 1 and a pharmaceutically acceptable carrier.

9. A method of inhibiting HIV integrase, comprising the administration to a mammal in need of such treatment a therapeutically effective amount of a compound of structural formula I:

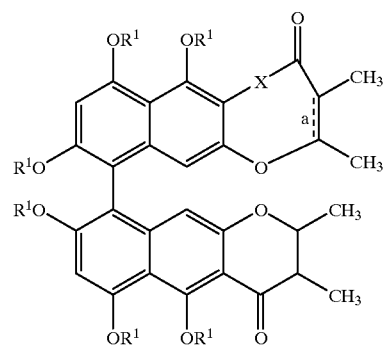

wherein:

$R^1$ is independently selected from:

(a) hydrogen, (b) $C_{1-6}$ alkyl, and (c) $C_{1-6}$ alkylcarbonylat each occurrence;

—X— is selected from:

(a) a carbon-carbon single bond, and (b) —O—; and the dotted line, a, represents a single bond or a double bond;

or a pharmaceutically acceptable salt thereof.

10. The method according to claim 9 wherein the compound of structural formula I is selected from:

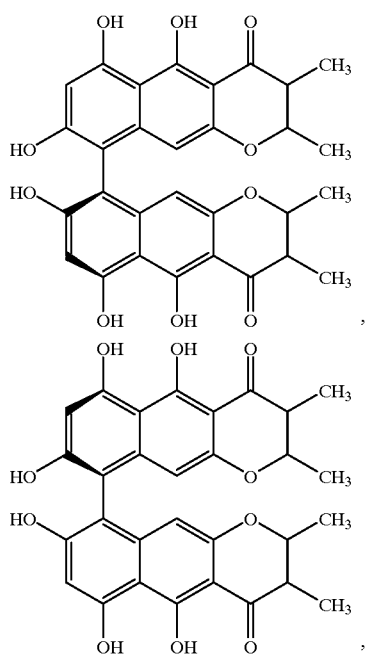

-continued

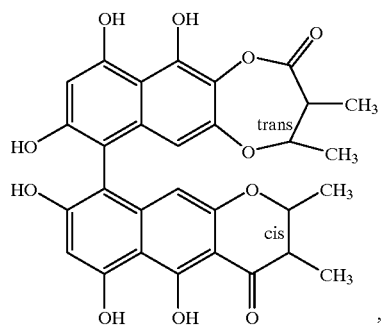

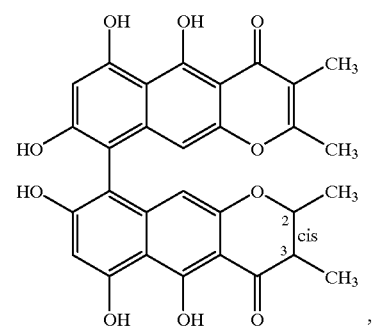

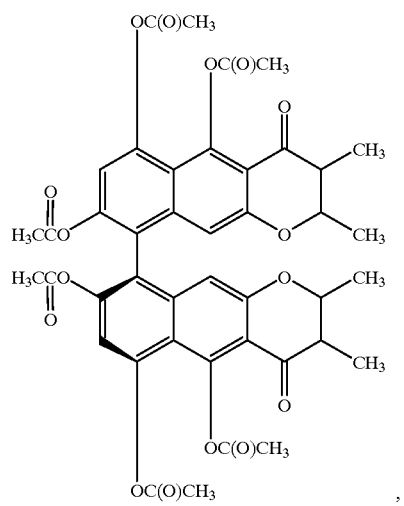

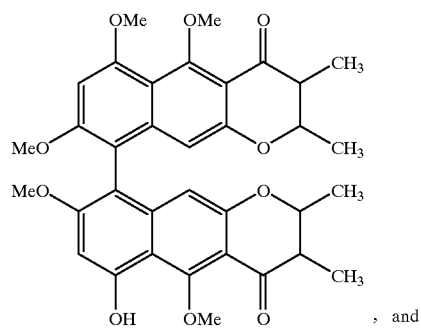

, and

-continued

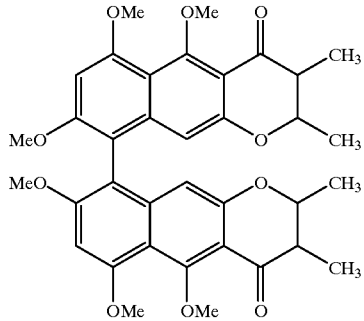

or a pharmaceutically acceptable salt thereof.

11. A method of treating infection by HIV, or of treating ADS or ARC, comprising the administration to a mammal in need of such treatment a therapeutically effective amount of a compound of structural formula I:

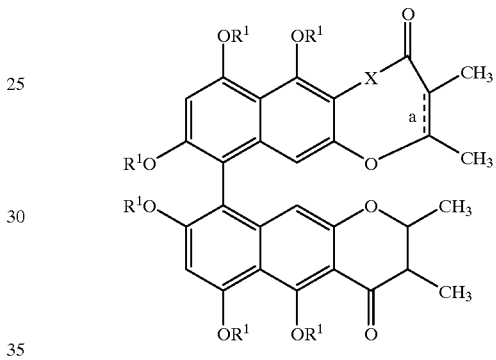

(I)

wherein:
  $R^1$ is independently selected from:
    (a) hydrogen,
    (b) $C_{1-6}$ alkyl, and
    (c) $C_{1-6}$ alkylcarbonyl-
  at each occurrence;
  —X— is selected from:
    (a) a carbon-carbon single bond, and
    (b) —O—; and
  the dotted line, a, is represents a single bond or a double bond;
or a pharmaceutically acceptable salt thereof.

12. The method according to claim 11 wherein the compound of structural formula I is selected from:

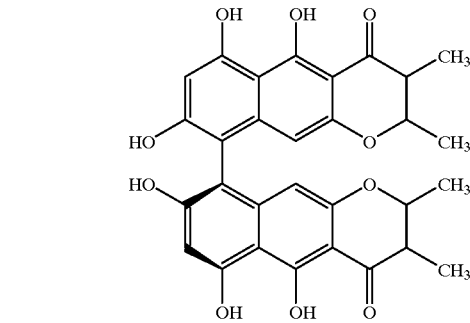

,

-continued
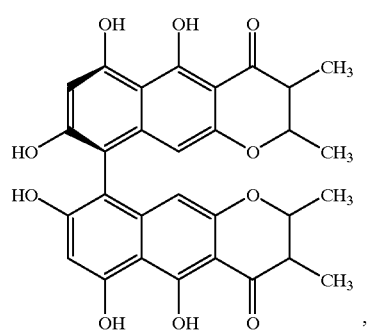,
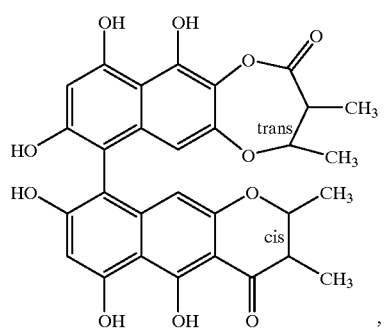,
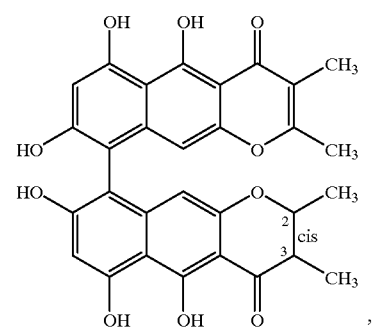,
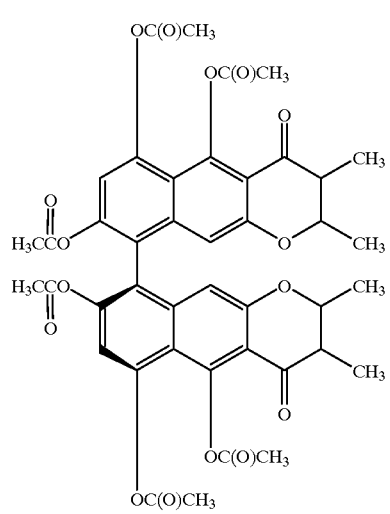,
-continued
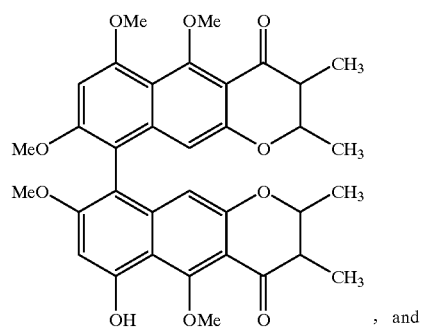, and
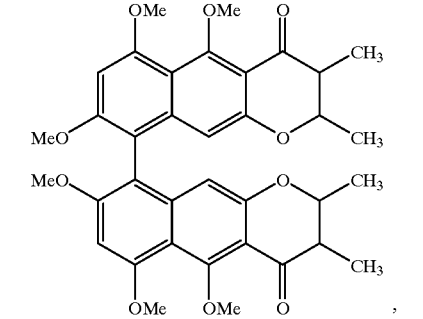
or a pharmaceutically acceptable salt thereof.
13. The method according to claim 12 wherein the compound of structural formula I is selected from:
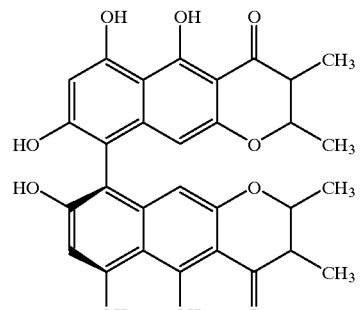
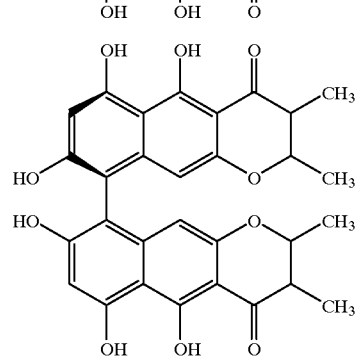

-continued

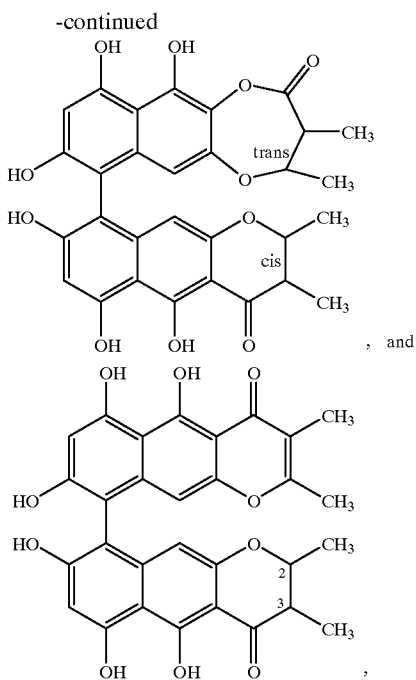

, and or a pharmaceutically acceptable salt thereof.

14. The method according to claim 11 additionally comprising the administration of a therapeutically effective amount of another AIDS treatment agent selected from:
   (a) an AIDS antiviral agent,
   (b) an immunomodulator, and
   (c) an anti-infective agent.

15. The method according to claim 14 wherein the AIDS antiviral agent is:
   N-(2(R)-hydroxy-l(S)-indanyl)-2(R)-phenylmethyl-4(S)-hydroxy-5-( 1-(4-(3-pyridylmethyl)-2(S)-N'-(t-butylcarboxamido)-piperazinyl))-pentaneamide or a pharmaceutically acceptable salt thereof.

16. A process for making a compound of claim 13, comprising cultivating MF6252 (ATCC 74396) under conditions suitable for the formation of the compound and recovering the compound.

17. A process for making a compound of claim 13 which comprises:
   (a) fermenting a culture of MF6252 (ATCC 74396), Fusarium sp. to produce a fermentation broth,
   (b) extracting the fermentation broth with an organic solvent,
   (c) isolating the compound of claim 13.

* * * * *